(12) United States Patent
Liu et al.

(10) Patent No.: US 11,703,475 B2
(45) Date of Patent: *Jul. 18, 2023

(54) METHOD OF USING INTEGRATED ELECTRO-MICROFLUIDIC PROBE CARD

(71) Applicant: TAIWAN SEMICONDUCTOR MANUFACTURING COMPANY, LTD., Hsinchu (TW)

(72) Inventors: Yi-Shao Liu, Zhubei (TW); Fei-Lung Lai, New Taipei (TW); Chun-Ren Cheng, Hsinchu (TW); Chun-Wen Cheng, Zhubei (TW)

(73) Assignee: TAIWAN SEMICONDUCTOR MANUFACTURING COMPANY, LTD., Hsinchu (TW)

( * ) Notice: Subject to any disclaimer, the term of this patent is extended or adjusted under 35 U.S.C. 154(b) by 433 days.

This patent is subject to a terminal disclaimer.

(21) Appl. No.: 16/588,088

(22) Filed: Sep. 30, 2019

(65) Prior Publication Data
US 2020/0025713 A1 Jan. 23, 2020

Related U.S. Application Data

(60) Continuation of application No. 15/350,399, filed on Nov. 14, 2016, now Pat. No. 10,429,341, which is a division of application No. 13/673,602, filed on Nov. 9, 2012, now Pat. No. 9,523,642.

(51) Int. Cl.
*G01N 27/414* (2006.01)
*G01N 21/75* (2006.01)
(Continued)

(52) U.S. Cl.
CPC .... *G01N 27/4145* (2013.01); *B01L 3/502707* (2013.01); *B01L 9/527* (2013.01);
(Continued)

(58) Field of Classification Search
CPC ................ G01N 27/4145; G01N 21/75; B01L 3/502707; B01L 9/527
See application file for complete search history.

(56) References Cited

U.S. PATENT DOCUMENTS 4,677,474 A * 6/1987 Sato ...................... H01L 21/682
324/750.22
10,429,341 B2 * 10/2019 Liu .................... B01L 3/502707
(Continued)

FOREIGN PATENT DOCUMENTS

CN 1421692 6/2003
CN 102549735 7/2012

OTHER PUBLICATIONS

Microfluidic probe: a new tool for integrating microfluidic environments and electronic wafer-probing. David A. Routenberg and Mark A. Reed Lab Chip, 2010, 10, 123-127 (Year: 2010).*
(Continued)

*Primary Examiner* — Lyle Alexander
*Assistant Examiner* — Dwan A Gerido
(74) *Attorney, Agent, or Firm* — Hauptman Ham, LLP

(57) ABSTRACT

A method includes mounting an integrated electro-microfluidic probe card to a device area on a bio-sensor device wafer, wherein the electro-microfluidic probe card has a first major surface and a second major surface opposite the first major surface. The method further includes electrically connecting at least one electronic probe tip extending from the first major surface to a corresponding conductive area of the device area. The method further includes stamping a test fluid onto the device area. The method further includes measuring via the at least one electronic probe tip a first electrical property of one or more bio-FETs of the device area based on the test fluid.

20 Claims, 6 Drawing Sheets

(51) Int. Cl.
  *G01N 33/543* (2006.01)
  *G01N 27/327* (2006.01)
  *B01L 3/00* (2006.01)
  *B01L 9/00* (2006.01)

(52) U.S. Cl.
  CPC ......... *G01N 21/75* (2013.01); *G01N 27/3275* (2013.01); *G01N 33/5438* (2013.01); *B01L 2200/025* (2013.01); *B01L 2200/027* (2013.01); *B01L 2200/10* (2013.01); *B01L 2200/143* (2013.01); *B01L 2300/0645* (2013.01); *G01N 27/3271* (2013.01); *Y10T 29/49* (2015.01)

(56) References Cited

U.S. PATENT DOCUMENTS

| | | | | |
|---|---|---|---|---|
| 2002/0164604 | A1* | 11/2002 | Abbott | B82Y 30/00 435/287.2 |
| 2002/0197895 | A1 | 12/2002 | Eldridge | |
| 2009/0155476 | A1* | 6/2009 | Francis | H01L 21/6704 118/300 |
| 2011/0141460 | A1* | 6/2011 | Buczkowski | G01N 21/6489 356/237.1 |
| 2013/0096033 | A1* | 4/2013 | Routenberg | C40B 50/06 506/26 |

OTHER PUBLICATIONS

Micropatterning of cell aggregate in three dimensions for in vivo mimicking cell culture Hidenori Otsuka Colloid and Interface Science in Pharmaceutical Research and Development 2014, 223-241 (Year: 2014).*

Routenberg, David A., et al., "Microfluidic Probe: A New Tool for Integrating Microfluidic Environments and Electronic Wafer-Probing", The Royal Society of Chemistry 2010, 123-127.

Surface Patterning Using Self Assembled Monolayers Rahul Bhure and Anil Mahapatra ACS Symposium Series; American chemical Society, 2010 (Year: 2010).

* cited by examiner

METHOD OF USING INTEGRATED ELECTRO-MICROFLUIDIC PROBE CARD

PRIORITY CLAIM

The present application is a continuation of U.S. application Ser. No. 15/350,399, filed Nov. 14, 2016, which is a divisional of U.S. application Ser. No. 13/673,602, filed Nov. 9, 2012, now U.S. Pat. No. 9,523,642, issued Dec. 20, 2016, which are incorporated herein by reference in their entireties.

FIELD

This disclosure relates to methods for forming and for testing biosensors on a chip. Particularly, this disclosure relates to systems and methods for testing biological field-effect-transistors (bioFETs) and methods for forming them.

BACKGROUND

Biosensors are devices for sensing and detecting biomolecules and operate on the basis of electronic, electrochemical, optical, and mechanical detection principles. Biosensors that include transistors are sensors that electrically sense charges, photons, and for mechanical properties of bio-entities or biomolecules. The detection can be performed by detecting the bio-entities or biomolecules themselves, or through interaction and reaction between specified reactants and bio-entities/biomolecules. Such biosensors can be manufactured using semiconductor processes, can quickly convert biomolecular information to electric signals, and can be easily applied to integrated circuits (ICs) and microelectromechanical systems (MEMS).

BioFETs (biological field-effect transistors, biologically sensitive field-effect transistors, biologically active field-effect transistors, or bio-organic field-effect transistors) are a type of biosensor that includes a transistor for electrically sensing biomolecules or bio-entities. While BioFETs are advantageous in many respects, challenges in their fabrication and/or operation arise, for example, due to compatibility issues between the semiconductor fabrication processes and biological applications.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion.

DETAILED DESCRIPTION

Figure 1:
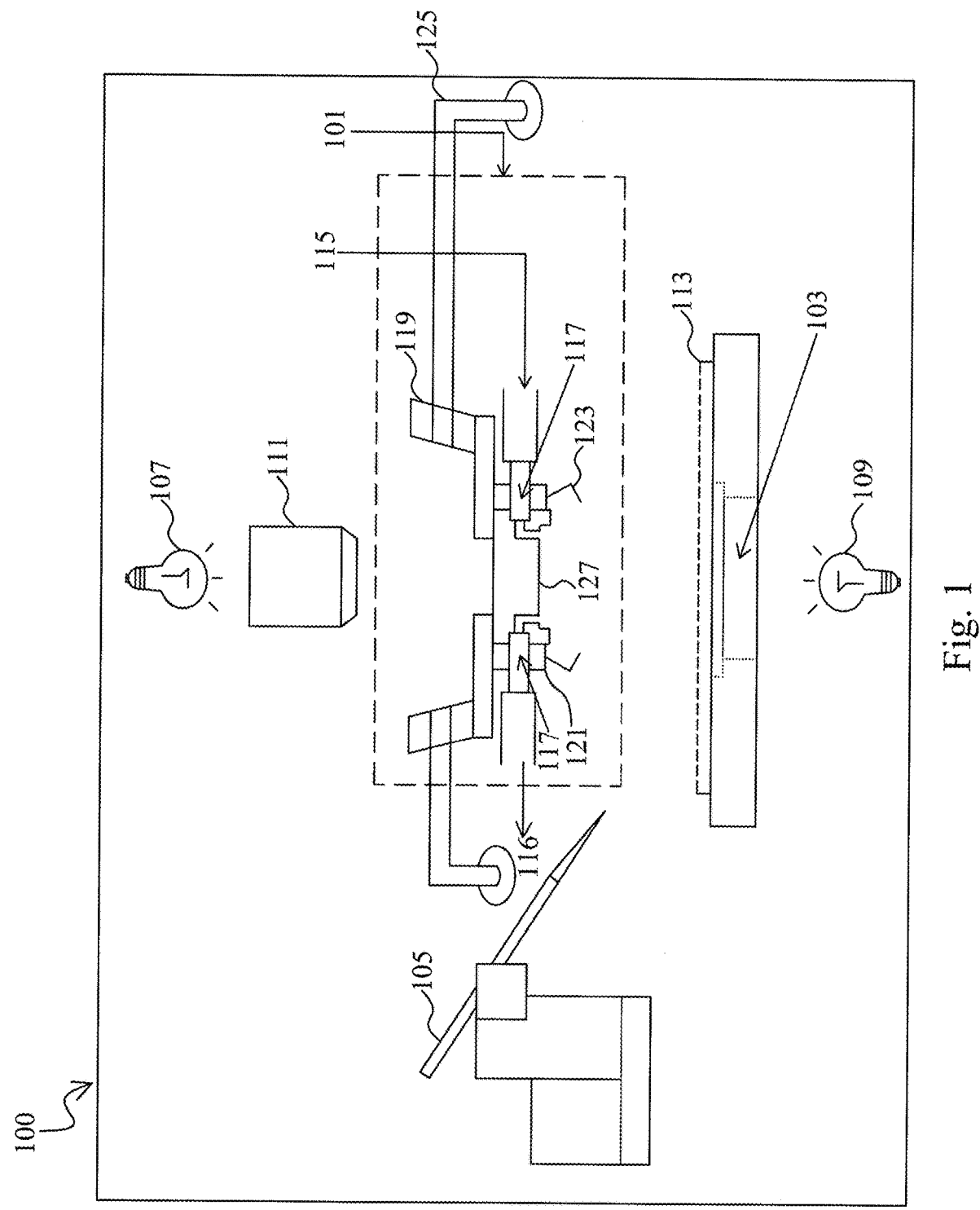
FIG. 1 is a schematic of an embodiment of a wafer-level biosensor processing tool according to one or more aspects of the present disclosure.

It is to be understood that the following disclosure provides many different embodiments, or examples, for implementing different features of the invention. Specific examples of components and arrangements are described below to simplify the present disclosure. These are, of course, merely examples and are not intended to be limiting. Moreover, the formation of a first feature over or on a second feature in the description that follows may include embodiments in which the first and second features are formed in direct contact, and may also include embodiments in which additional features may be formed interposing the first and second features, such that the first and second features may not be in direct contact. Further still, references to relative terms such as "top", "front", "bottom", and "back" are used to provide a relative relationship between elements and are not intended to imply any absolute direction. Various features may be arbitrarily drawn in different scales for simplicity and clarity.

In a biological field-effect transistor (BioFET), the gate of a metal-oxide-semiconductor field-effect transistor (MOSFET), which controls the conductance of the semiconductor between source and drain contacts, includes a bio- or bio-chemical-compatible layer or a biofunctionalized layer of immobilized probe molecules that act as surface receptors. Essentially, a BioFET is a field-effect biosensor with a semiconductor transducer. An advantage of BioFETs is the prospect of label-free operation. Specifically, BioFETs enable the avoidance of costly and time-consuming labeling operations such as the labeling of an analyte with, for instance, fluorescent or radioactive probes. When a labeled analyte reacts as designed and emits fluorescence or radio-activity, the emission is short-lived and thus has a short measurement window of opportunity. However, even with these cost, time-consumption, and design constraints, use of the labeled analyte provides a good quantification of a reaction and may be appropriate in some circumstances, for example, for benchmarking a new biosensor.

A typical detection mechanism for BioFETs is the conductance modulation of the transducer due to the binding of a target biomolecule or bio-entity to a sensing surface or a receptor molecule immobilized on the sensing surface of the BioFET. When the target biomolecule or bio-entity is bonded to the sensing surface or the immobilized receptor, the drain current of the BioFET is varied by the potential from the sensing surface. This change in the drain current can be measured and the bonding of the receptor and the target biomolecule or bio-entity can be identified. Many biomolecules and bio-entities may be used to functionalize the sensing surface of the BioFET such as ions, enzymes, antibodies, ligands, receptors, peptides, oligonucleotides, cells of organs, organisms and pieces of tissue. For instance, to detect ssDNA (single-stranded deoxyribonucleic acid), the sensing surface of the BioFET may be functionalized with immobilized complementary ssDNA strands. Also, to detect various proteins such as tumor markers, the sensing surface of the BioFET may be functionalized with monoclonal antibodies.

One difference in various types of BioFETs is the location of the sensing surface. One example of a sensing surface is a top of a floating gate connected to the gate of the BioFET. In other examples of sensing surfaces, the biomolecules bind directly or through receptors on the gate or the gate dielectric of the BioFET. These BioFETs directly sense the target biomolecules and are more accurate than those having a sensing surface on a floating gate.

A BioFET device may include a number of BioFETs and other transistors and circuitry. Each of the BioFETs has a sensing surface associated with a microfluidic channel or well where a biological matter may flow and be sensed. A BioFET device may be manufactured by several entities and assembly/testing may be performed by yet other entities. In a typical scenario, the transistors including BioFETs and non-bio FETs are manufactured on a semiconductor substrate in a semiconductor manufacturing fabrication facility using complementary metal-oxide-semiconductor (CMOS) process compatible techniques. In some embodiments, the microfluidic structures on the BioFET device are formed directly on the substrate after the transistors and circuits are formed. In some embodiments, the microfluidic structures on the BioFET device are formed separately and attached at the semiconductor manufacturing fabrication facility. In some embodiments, the microfluidic structures on the BioFET device are formed separately and attached at another facility, which may be a customer or a vendor of the semiconductor manufacturing fabrication facility.

A semiconductor manufacturing fabrication facility is equipped to perform chip level, wafer level, and wafer level chip scale testing for the semiconductor devices produced at the fabrication facility. A general semiconductor probe station usually includes micromanipulators or probe cards for electrical probing of a partially or fully fabricated device. If any defects are found, the product may be reworked or marked before shipping. However, traditional semiconductor probe stations are not equipped to test BioFET devices under operating conditions. While the basic electrical properties may be tested, the portions of the BioFET devices used with biological fluids, such as sensing surfaces and microfluidic channels, cannot be tested using a traditional semiconductor probe station.

In a biological laboratory, a sample delivery system usually uses an array of pipette tips or a printer head to transfer biological samples onto a specimen on a target with fixed dimensions, for example, a 96 well-plate. One or more fluid supplies are connected to delivery pipettes that inject the fluid into a container, usually a test tube or wells on a plate. Either the container or the pipettes move relative to the other. A sample delivery system may involve several pipettes that can simultaneously deliver fluid to multiple containers. Some pipettes may also pick up fluid from one container and deliver the fluid to another container.

The present disclosure provides a system for wafer level chip scale post-processing and testing of BioFET devices, such as a Lab-On-Chip device. The ability to verify functionality and yield of a BioFET device without shipping for testing to be performed at a customer site and resultant delays makes mass production of biomedical devices in a semiconductor foundry possible. A wafer-level biosensor processing tool can integrate post-processing (sensing surface functionalization, sample delivery) and testing (optical probing for fluidic dynamics and biological reactions; electrical probing for device characteristics). The wafer-level biosensor processing tool can monitor the biological reactions via an attached microscope in real-time. The wafer-level biosensor processing tool allows testing and diagnostics/trouble shooting, if a problem is detected. The wafer-level biosensor processing tool also expedites feedback to the manufacturer of BioFET devices.

The present disclosure provides a wafer-level biosensor processing tool that combines the various functions for electrical and biological processing and testing on one platform. FIG. 1 is a schematic diagram of a wafer-level biosensor processing tool 100 in accordance with various embodiments of the present disclosure. The wafer-level biosensor processing tool 100 may be enclosed in a chamber to allow for environmental control. For example, the various processing and testing may be performed in a temperature or pressure environment different from the ambient. The chamber may include gas inlets and outlets to control an atmospheric composition during processing and testing. For mass production, load locks and automated wafer carrier/cassette handling may also be incorporated into the wafer-level biosensor processing tool 100.

When a wafer enters the wafer-level biosensor processing tool 100, the BioFETs and circuitry are already formed. A wafer 113 is positioned on a wafer stage 103 in the tool 100. The wafer 113 is shown in dotted lines because it is not a part of the wafer-level biosensor processing tool 100 during a non-operating state. The wafer 113 may be positioned by a wafer transfer robot arm (not shown) or the wafer may be manually placed by an operator. The wafer stage 103 is at least partially transparent, to allow light from a light source 109 to transmit light through the wafer stage during operation. The wafer stage 103 may be a pedestal, a susceptor, or a carousel where more than one wafer or workpiece may be processed or tested at the same time. The wafer stage 103 may be moved in one or many directions. According to various embodiments, the wafer stage 103 has freedom of motion in at least 2 directions: x and y. In some embodiments, the wafer stage 103 may be moved in 3 directions x, y, and z; x, z, and e (theta) (rotational); or x, y, and e (rotational). The wafer stage 103 may also include an embedded temperature control including sensors and a heater/cooler configured to change the temperature of the wafer 113 by conductive heating or cooling. In some embodiments, the wafer stage 103 may accommodate a portion of a wafer (partially diced), a die, a number of dies on a package substrate, or a packaged chip.

Figure 2:
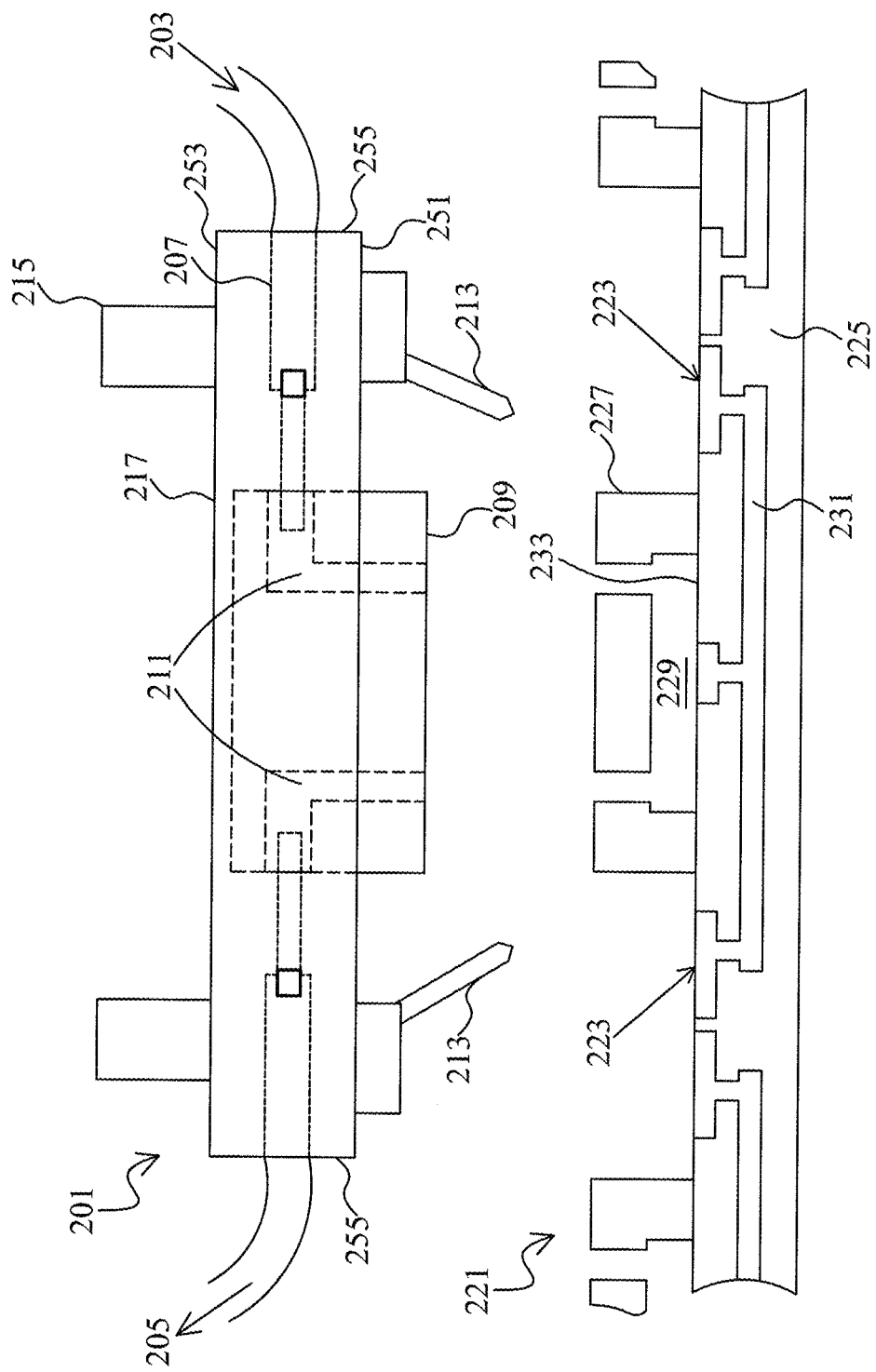
FIG. 2 is cross-sectional views of an integrated electro-microfluidic probe card and portion of a BioFET according to one or more aspects of the present disclosure.
Figure 3:
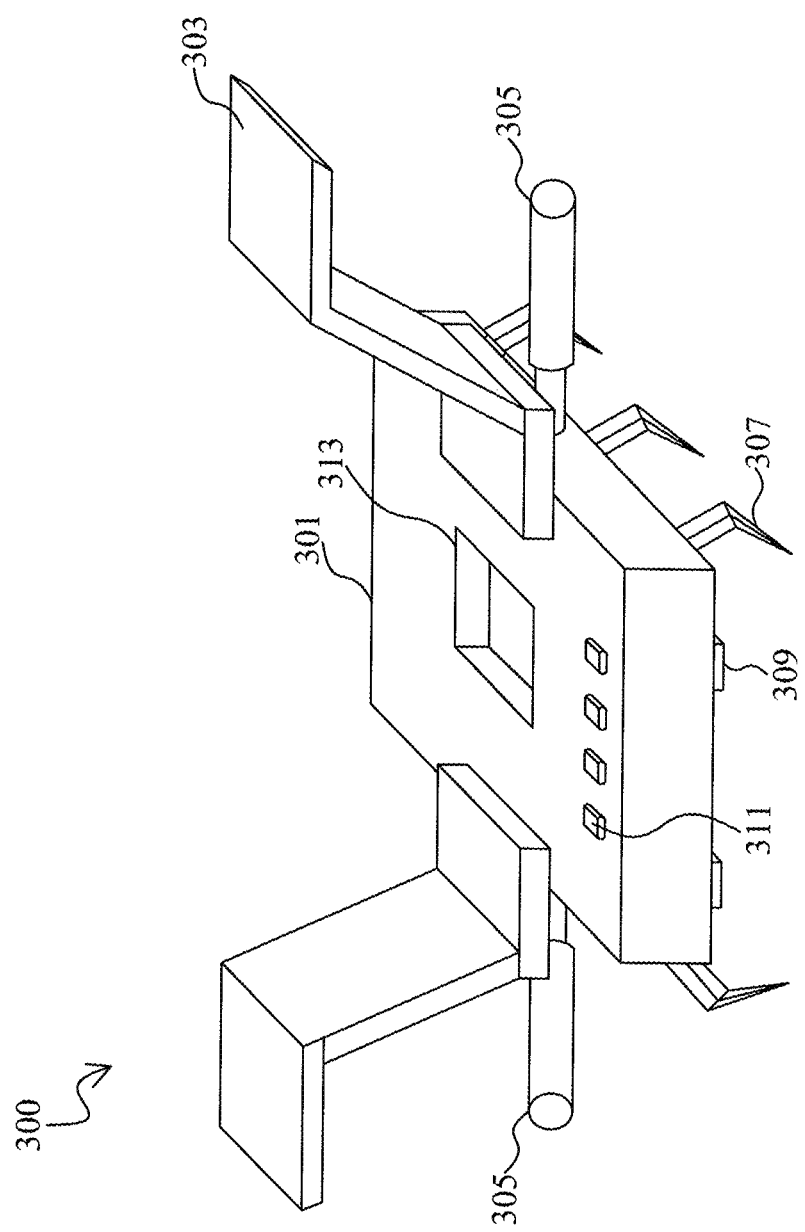
FIGS. 3 and 4 are perspective views of integrated electro-microfluidic probe cards according to one or more embodiments of the present disclosure.
Figure 4:
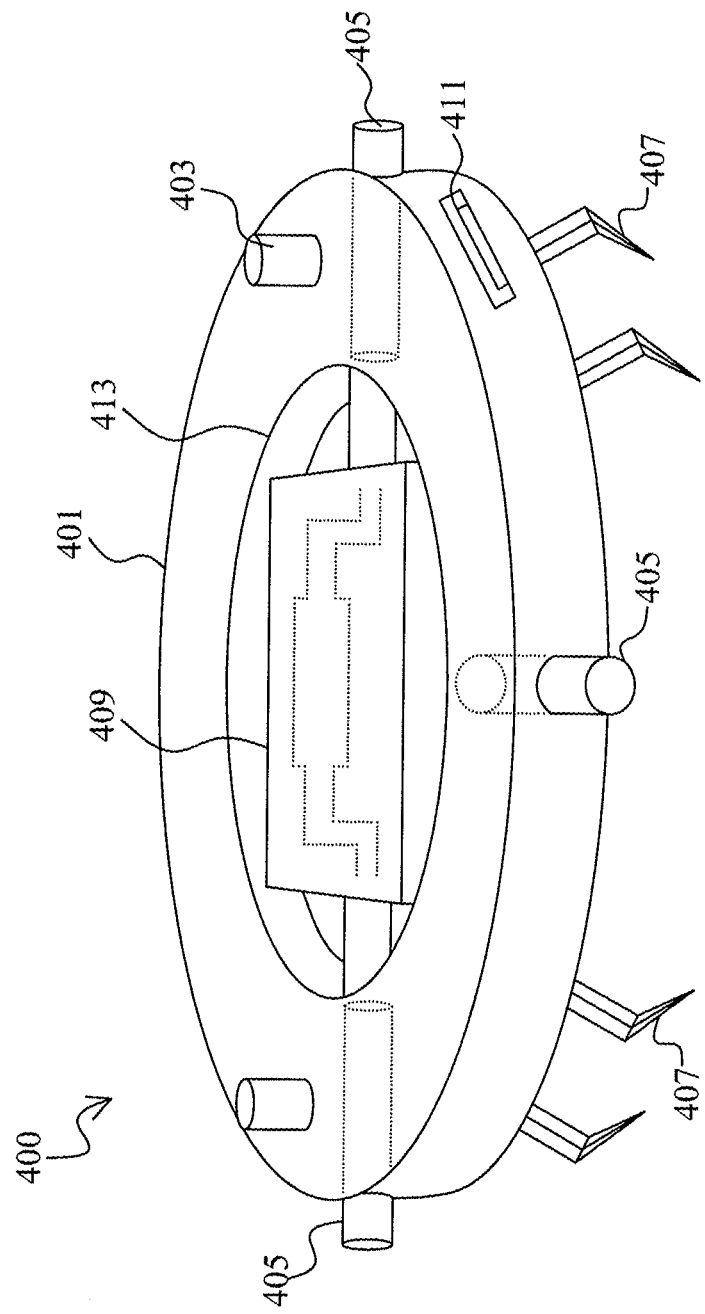

The wafer-level biosensor processing tool 100 also includes an integrated electro-microfluidic probe card 101 positioned over the wafer stage 103. The integrated electro-microfluidic probe card 101 includes a fluidic mount 121 containing one or more fluidic probes 127 and one or more electrical probes 123. The fluidic mount 121 includes at least one set of fluid inlet and outlet 117 that accepts test fluid or process fluid from a fluid supply 115 and returns used fluid to a fluid return 116. FIGS. 2-4 show different embodiments of the integrated electro-microfluidic probe card and various features of the integrated electro-microfluidic probe card will be discussed in more detail.

The integrated electro-microfluidic probe card 101 also includes one or more handle lugs 119 attached to an edge portion or a side portion of the integrated electro-microfluidic probe card 101. The integrated electro-microfluidic probe card 101 may be held and moved by one or more card fixture arms 125 or by a micromanipulator arm using one or more of the handle lugs 119. During operation, the card fixture arms 125 exert downward pressure on the integrated electro-microfluidic probe card 101 so that the fluidic probe 127 seals against the wafer 113. Thus, the card fixture arm 125 is configured to move the integrated electro-microfluidic probe card 101 in at least a downward direction. According to various embodiments, the card fixture arm 125 has movable joints and/or a base capable of moving laterally as well as vertically.

According to various embodiments, the integrated electro-microfluidic probe card 101 is at least partially transparent such that a microscope 111 positioned over the integrated electro-microfluidic probe card 101 may observe bio-reactions on the wafer 113 through the fluidic mount 121. The handle lugs 119 are positioned so as not to obstruct the propagation of light to microscope 111. At least a portion of the fluidic mount 121 over the fluidic probe 127 is transparent. Light source 107 over the microscope 111 can be used to illuminate the wafer through the integrated electro-microfluidic probe card 101 or to trigger fluorescence or phosphorescence by radiating labels in the analyte with light at a specific wavelength.

The microscope 111 may be mounted to a camera capable of recording and measuring various optical aspects of an image captured using the microscope. Further, the microscope 111 may be moved independently from the wafer stage 103 and the integrated electro-microfluidic probe card 101 so as to focus on just a portion of a viewable area of the wafer stage through the transparent fluidic mount 121.

The wafer-level biosensor processing tool 100 also includes one or more micromanipulators 105 that can hold various probing tools, for instance, needles, scribes, nozzles, pipette tips or electrodes. Through the probing tools, small quantities of processing fluid or testing fluid may be added or extracted from the wafer 113. The micromanipulators 105 may be controlled through an operator interface and has enough precision of movement to target a small area of a BioFET device being diagnosed. For example, if a BioFET fails a test, a small amount of etchant may be added to remove a layer from a surface of the wafer or to remove a portion of a sensing surface to further diagnose the reason for the failure. The micromanipulator 105 may work in concert with the microscope 111. For example, the micromanipulator 105 may be calibrated by dropping a fluid at a specified area on the wafer stage 103, the drop may be verified automatically by the camera attached to the microscope 111. In another example, an operator may remove a portion of a layer of material by sawing or scribing with the micromanipulator 105 and verify the results by viewing through the microscope 111.

FIG. 2 includes cross-section diagrams of an integrated electro-microfluidic probe card 201 and a portion 221 of the wafer 113. The integrated electro-microfluidic probe card 201 includes a fluidic mount 217. The fluidic mount 217 has a major surface 251 facing the wafer portion 221 and another major surface 253 facing away from the wafer portion 221. One or more electric probes 213 and one or more fluidic probes 209 are formed or mounted on the major surface 251. One or more handle lugs 215 is formed or mounted on the other major surface 253 near the edges or on a minor surface 255 so as to not obstruct a view of the wafer portion 221 from the major surface 253. At least one electronic port (not shown), at least one fluid input 203 and at least one fluid output 205 are disposed on the minor surfaces 255. The use of words "major" and "minor" does not imply that the surface area of a major surface is necessarily larger than that of a minor surface. Rather, the words are used to distinguish surfaces that either face toward or away from the wafer and the surfaces that are normal to the wafer.

The electric probe 213 includes an electronic probe tip of a conducting material and a base for supporting the electronic probe tip and for electrically connecting the electronic probe tip to the electronic port on the fluid mount 217. The electronic probe tip may be made of a metal and may comprise a flexible material or a joint. The conducting material at the electronic probe tip is configured to make electrical contact with a contact pad 223 on a surface of the wafer portion 221 using a contact area smaller than the area of the contact pad 223.

Internal to the fluidic mount 217 are microfluidic channels 207 that routes fluids from the fluidic input 203 through the fluidic probe 209 to the fluidic output 205. Microfluidic channels 207 may include valves, pumps, heaters, or other devices in contact with the fluid that can control or direct the fluid. Other devices may include various electrodes that can increase, decrease, or deflect flow of the fluid. Examples are magnets or ferromagnets or electrodes for magnetophoresis, metal electrodes for electrophoresis, or particular dielectric material for dielectrophoresis. The valves, pumps, and heaters may be microelectromechanical systems (MEMS). The microfluidic channels 207 may also include various sensors or microsensors such as pressure sensors, flow meters, temperature sensors, and electrical sensors coupled to the fluid flow.

The fluidic probe 209 includes conduits 211 for conducting fluid to and from the wafer portion 221 to be tested. During testing or processing, the integrated electro-microfluidic probe card 201 is positioned over the wafer portion 221 so that the electric probes 213 on the integrated electro-microfluidic probe card 201 are aligned with the metal pads 223 on the wafer portion 221 and the fluidic probe 209 is aligned with a BioFET well 229 on the wafer portion 221. The integrated electro-microfluidic probe card 201 is then mounted with the wafer 221 either by moving the wafer stage up or lowering the integrated electro-microfluidic probe card 201 to create a seal between the fluidic probe 209 and the BioFET well 229. In order to create a seal, the fluidic mount 217 and/or the fluidic probe 209 may deform. However, the fluidic mount 217 and the fluidic probe 209 are designed to return to their original shape after dismounting from the wafer so they may be re-used.

The fluidic mount 217 and the fluidic probe 209 may be formed of silicone, epoxy, or photoresist. In some embodiments, the fluidic mount 217 and the fluidic probe 209 may be formed of polydimethylsiloxane (PDMS) or polymethylmethacrylate (PMMA). In certain embodiments, the fluidic mount 217 and the fluidic probe 209 are made of the same material, which is bio-compatible and may be re-usable. In some embodiments, the material is molded.

The wafer portion 221 is formed on a substrate 225 which includes interconnect structure 231 having electrical contact pads 223 and sensing surface 233 within a microfluidic structure 227 enclosing a microfluidic well 229. The microfluidic structure 227 is formed above the sensing surface 233. In some embodiments, the microfluidic structure 227 may have different shapes depending on the placement of the sensing surface 233. For example, in some embodiments, the sensing surface 233 is at or close to a gate of a BioFET; allowing the microfluidic structure 227 to be embedded in the interconnect structure.

In some embodiments, a fluidic mount template is formed having the various electric probes, electronic port, fluid input and outputs, and handle lugs. Recesses on the same side of the electric probes are prepared. The fluidic probe inserts are designed to complement the design of the microfluidic structure on the BioFET device. For example, if a well structure having inlet and outlet is available on the BioFET device, then a conduit type fluidic probe such as fluidic probe 209 of FIG. 2 is used. If no microfluidic structure is available on the BioFET device, then a well-type fluidic probe is used, where the fluidic probe surrounds and covers the sensing surface on the BioFET. Using recesses on a fluidic mount allows the same fluidic mount to be used for more than one BioFET device layout. Using recesses also allows the fluidic probes to be removed for cleaning. In other embodiments, the microfluidic mount and the fluidic probes are formed for each BioFET device.

The wafer portion 221 may include one BioFET device, a portion of a BioFET device, or multiple BioFET devices. In some embodiments, the integrated electro-microfluidic probe card 201 has many fluidic probes and electronic probes at different locations to test more than one BioFET device with one integrated electro-microfluidic probe card simultaneously. On the other hand, a simple integrated electro-microfluidic probe card 201 with one or a few fluidic probes and one or a few electronic probes may be used to test similarly dimensioned BioFET devices separately. In one example, an integrated electro-microfluidic probe card has a fluidic mount having recesses for the fluidic probes. Depending on the number of BioFETs to be tested and the locations of the BioFETs, the recesses may be configured with a fluidic probe or a blank flange that covers the recesses where no testing is intended. In some embodiments, additional electronic probes are added or removed. Such integrated electro-microfluidic probe card may be a generic card capable of testing different BioFET devices.

FIGS. 3 and 4 are both perspective views of integrated electro-microfluidic probe card embodiments 300 and 400. In FIG. 3, the integrated electro-microfluidic probe card 300 includes fluidic mount 301 having a window 313 through which the microscope 111 (FIG. 1) may record or observe reactions. Because an observation window is used, the fluidic mount 301 may or may not be transparent. Handle lugs 303 are attached on a top surface of the fluidic mount 301. Electronic ports 311 are also formed on the top surface of fluidic mount 301. In other embodiments, the handle lugs and the electronic port may be on a minor surface normal to the wafer 113 (FIG. 1). Fluid input and output 305 is formed on the minor surface. Even though only one fluid input and output are shown on each minor surface, additional fluid inputs and outputs on the fluid mount 301 are possible. Further, the fluid input and output 305 may be on the same side or different sides of the fluid mount 301. On the major surface closest to the wafer, fluidic probes 309 and electronic probes 307 are disposed. In some embodiments, the electronic probes 307 are flexible to make reliable electrical contact with the contact pads 223 (FIG. 2) on the wafer. In certain embodiments, the electronic probes may be mechanically actuated to contact different contact pads 223 on the wafer through movement of one or more joints on a micromanipular arm. In addition to sensing electrical properties, the electronic probes may be used to provide a bias voltage or a current.

In FIG. 4, the integrated electro-microfluidic probe card 400 includes fluidic mount 401 having a window 413 through which the microscope 111 (FIG. 1) may record or observe reactions. Because an observation window is used, the fluidic mount 401 may or may not be transparent. In the embodiment of FIG. 4, the fluidic probe 409 is transparent to allow observation. Handle lugs 403 are attached on a top surface of the fluidic mount 401 in this embodiment. In other embodiments, the handle lugs 403 are attached on a minor surface normal to the wafer 113 (FIG. 1). In some embodiments, fluid input and outputs 405 and electronic port 411 are formed on the minor surface of fluidic mount 401. Even though three fluid input and outputs 405 are shown, additional fluid input outputs are possible, in some embodiments. The fluidic mount 401 in this embodiment is in the shape of a cylinder and has only one minor surface. On the major surface closest to the wafer 113, one or more fluidic probes 409 and electronic probes 407 are disposed. In some embodiments, the electronic probes 407 are flexible to make reliable electrical contact with the contact pads 223 (FIG. 2) on the wafer. In certain embodiments, the electronic probes 407 are mechanically actuated to contact different contact pads on the wafer 113 through movement of one or more joints on a micromanipular arm. In addition to sensing electrical properties, the electronic probes 407 may be used to provide a bias voltage or a current.

Figure 5:
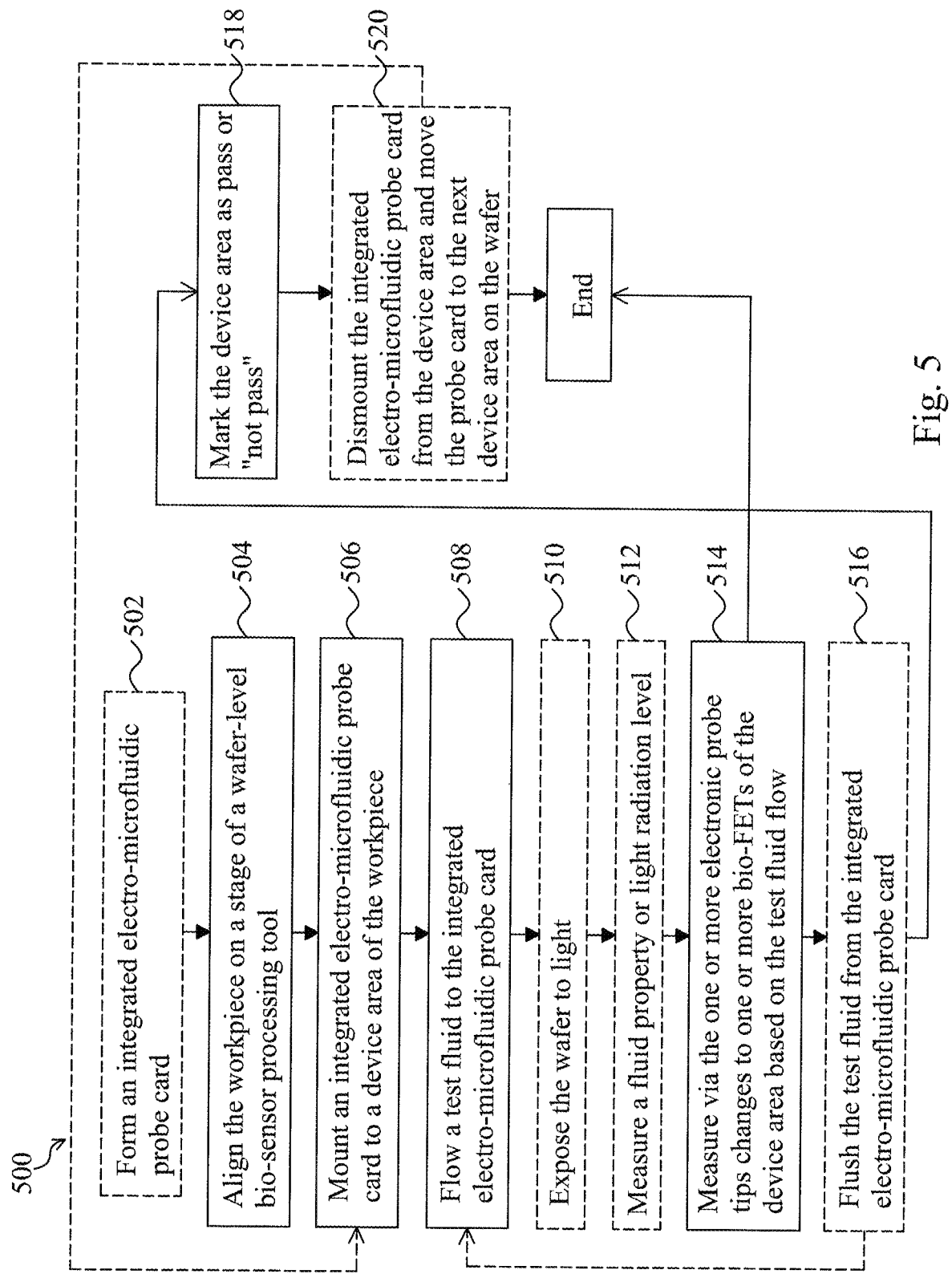
FIGS. 5 and 6 are flow charts of method embodiments for testing and fabricating a BioFET device according to various aspects of the present disclosure.
Figure 6:
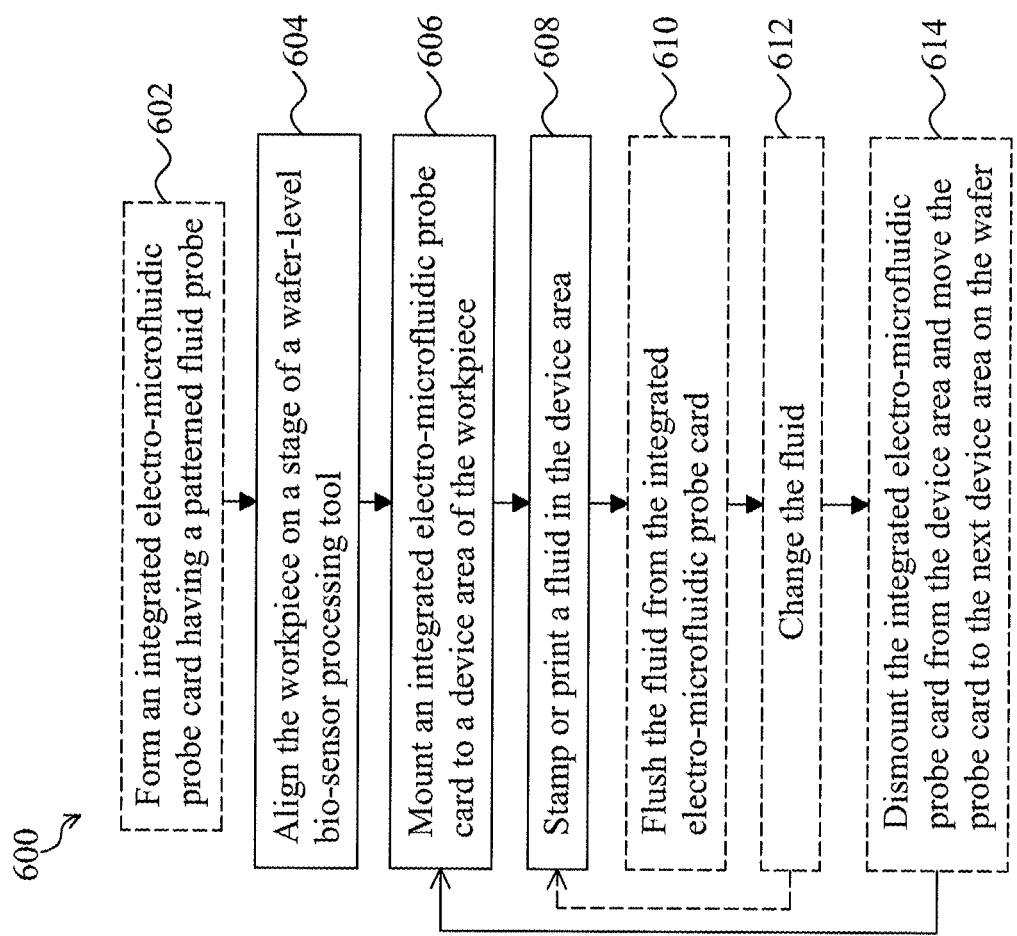

FIGS. 5 and 6 are process flow diagrams for testing and processing a partially or fully fabricated BioFET device in accordance with various embodiments of the present disclosure. FIG. 5 is process flow diagram of method 500 for testing a partially fabricated or fully fabricated BioFET device. In operation 502 an integrated electro-microfluidic probe card is formed. This operation may be performed by the facility testing the BioFET device, which also may be the same facility that manufactured the BioFET device. The integrated electro-microfluidic probe card may also be formed by a separate facility, for example, a customer of the manufacturer. As discussed, the integrated electro-microfluidic probe card may include various operational mechanisms (for example, MEMS) to allow for diagnostic examination in addition to testing.

In operation 504, the workpiece is aligned on a stage of a wafer-level biosensor processing tool. The workpiece includes the partially fabricated or fully fabricated BioFET device. The workpiece may be in the shape of a wafer, a portion of a wafer (partially diced), a die, a number of dies on a package substrate, or a packaged chip. While the descriptions of a wafer-level biosensor processing tool herein focuses on wafer processing, the concepts discussed may be applied to other workpiece shapes and types. In some embodiments, the alignment is confirmed optically or mechanically using an alignment mark or indentation on the workpiece.

In operation 506, an integrated electro-microfluidic probe card is mounted to a device area of the workpiece. As discussed, the mounting includes either the integrated electro-microfluidic probe card moving toward the workpiece or the workpiece to moving toward the integrated electro-microfluidic probe card. When mounted, the one or more fluidic probes on the integrated electro-microfluidic probe card seals against a portion of the device area of the workpiece, usually at a sensing surface, e.g., sensing surface 233 (FIG. 2), that may or may not include contact at a microfluidic structure. Further, electronic probes, e.g., electronic probes 213 (FIG. 2), on the integrated electro-microfluidic probe card also makes electrical contact with contact pads on workpiece.

In operation 508, a test fluid to flowed to the integrated electro-microfluidic probe card. In some embodiments, the test fluid is flowed through one or more fluid inputs, e.g., fluid input 203 (FIG. 2). The test fluid may include a biological matter or a proxy for a biological matter to test the BioFETs. The various flow mechanisms on the integrated electro-microfluidic probe card may pump and direct the test fluid toward one or more microfluidic wells or channels having the sensing surface. Further, in operations 510 and 512 the wafer may be exposed to light and a fluid property or light radiation level may be measured through a transparent fluidic mount or an observation window in the fluidic mount. For example, two test fluids may be added and mixed in a microfluidic well over the sensing surface. A microscope, e.g., microscope 111 (FIG. 1), may record the extent of the reaction by measuring a light radiation level at a particular frequency, for example, the reaction may result in a photon emission after irradiation that are measured by the microscope through the transparent fluidic mount or through the observation window.

In operation 514, changes to one or more BioFETs based on the test fluid flow are measured via the one or more electronic probe tips. The test fluid includes material that when attached to the sensing surface, changes the electrical properties of the BioFET. The electronic probe tips may measure a current or a voltage while optionally applying a voltage or current. In some embodiments, the electronic probe tip senses a difference in current through the BioFET before and after the test fluid flow. The sensed change is compared against an expected result as designed and may also be compared against an expected result based on the optical measurement from the microscope. If the sensed change matches the expected results, then the BioFET device performed properly as designed and manufactured and passes the test.

In some embodiments, the electronic probe tip provides power to the BioFET device for the BioFET device to conduct testing and analysis of the test fluid. The test results are provided to the wafer-level biosensor processing tool and compared against the expected results. In this case, signal processing and further operation are performed by the BioFET device before the test result is provided. The BioFET device may be pre-programmed with a number of the testing and analysis programs that are activated by the wafer-level biosensor processing tool, depending on the objective of the test. For example, one test may focus on the ability of the sensing surface to retain receptors. A test fluid that includes a marker or stain detectable by microscope with a high affinity for the receptors may be used to test the sensing surface. The microscope data is compared against the data from the electronic probe tips to verify whether the receptors are attached to the sensing surface. Another test may focus on the sensitivity of the transistor gate to a small change in a number of bound markers. Many test programs may be devised and results can be used to adjust the BioFET device design and/or the manufacturing process.

In operation 516, the test fluid may be flushed from the integrated electro-microfluidic probe card after testing and reading. The flush may include vacuuming, adding a stream of cleaning fluid, for example, deionized water, an inert fluid, or gas, and drying. In some cases when biological material is used for testing, the fluidic channels in the fluidic mount and the BioFET device are rinsed and cleaned before further processing. Some receptors on the sensing surface may require wetting or other preservation technique to prevent degradation or detachment during shelving or shipping.

In operation 518, the BioFET device may be marked as pass or "not pass" based on the performance of the BioFET during the testing process. The marking may be physical by scribing or otherwise making a mark on the BioFET device. The marking may also be not physical, for example, by noting the lot and location of the defect into a database. A marked BioFET device may undergo further processing to correct a detected problem, if possible, or be removed from the manufacturing process.

In operation 520, the integrated electro-microfluidic probe card is dismounted from the device area and moved to the next device area. If the integrated electro-microfluidic probe card has already tested all the devices on the wafer, then the integrated electro-microfluidic probe card moved to a home position away from the wafer. In some embodiments, only certain test devices on the wafer are used for method 500. For example, some BioFET device designs are intended as single-use and testing would be limited to a few test BioFET devices on the wafer that represent the yield of the rest of the wafer. For more complex designs that are re-usable or to verify the manufacturing process, every BioFET device may be tested.

The method 500 includes some optional operations. For example, the operation 502 of forming the integrated electro-microfluidic probe card may be performed by another facility. In some cases, a generic integrated electro-microfluidic probe card may be used. Operations 510 and 512 of using optical measurements may be omitted if a marker used is not photo-luminescent or has other photo-detectible characteristic, such as staining. Flushing the test fluid from the BioFET device and the integrated electro-microfluidic probe card may be omitted if the BioFET is a single use BioFET. After dismounting the integrated electro-microfluidic probe card from the wafer, the integrated electro-microfluidic probe card may not move to another location on the test workpiece. As discussed, the workpiece may not be a whole wafer having many devices thereon.

The method 500 includes some optional loops. For example, more than one test may be performed by flowing different test fluid or changing the test fluid flow properties after operation 516 by following the dotted line back to operation 508. More than one device area may be tested after operation 520 by following the dotted line to operation 506.

In addition to testing, the wafer-level biosensor processing tool may also be used to perform some processing such as building desirable chemistry on sensing surfaces, such as coating and attaching receptors, and on other flow surfaces in the microfluidic structure. FIG. 6 is a process flow diagram of method 600 for post fabrication processing on BioFET devices. In operation 602, an integrated electro-microfluidic probe card is formed. As discussed, the integrated electro-microfluidic probe card may include various operational mechanisms (for example, MEMS).

In operation 604, the workpiece is aligned on a stage of a wafer-level biosensor processing tool. The workpiece includes the partially fabricated or fully fabricated BioFET device. The workpiece may be in the shape of a wafer, e.g., wafer 113 (FIG. 1), a portion of a wafer, e.g., wafer portion 221 (FIG. 2) (partially diced), a die, a number of dies on a package substrate, or a packaged chip. The alignment may be confirmed optically or mechanically using an alignment mark or indentation on the workpiece. In operation 606, an integrated electro-microfluidic probe card is mounted to a device area of the workpiece. This operation is the same as operation 506 of FIG. 5.

In operation 608, a fluid is stamped or printed in the device area of the workpiece. In some embodiments, the fluidic probe forms a seal on the device area surface to effectively form a pattern on the surface when a fluid flows through the fluidic probe. The fluidic probe may include additional patterns on the surface of the fluidic probe contacting the device area. One or more fluids may be applied alternatingly or serially to achieve a desirable chemistry. In certain embodiments, the fluidic probe may include nozzles similar to a printer head that can release a set amount of fluid in an area defined by the fluidic probe. In one example, a self-aligned monolayer of receptors may be applied by printing onto a device area surface. In yet other embodiments, a stamping effect is achieved by patterning a surface of the fluidic probe such that one or more portions of the surface is wettable by a fluid and other portions of the surface are not wettable. The fluidic probe surface is then exposed to the fluid and the patterned transferred to the device area surface by stamping. Another stamping effect may be to use a fluid permeable material as the fluidic probe surface and patterning a portion of the surface so that it is not permeable by the fluid. One example is to use a porous dielectric material as the fluidic probe surface and coating a portion of it in a pattern with a non-porous material. When the fluid flows through the integrated electro-microfluidic probe card that is mounted on the device area, the fluid flows through the porous material and imprints a pattern on the device area surface. One skilled in the art may design a fluid probe that can stamp or print a pattern onto a device area using one or more of the techniques discussed or other techniques known to one skilled in the art.

In operation 610, the fluid may be flushed from the integrated electro-microfluidic probe card. As discussed in association with operation 516 of FIG. 5, a flush may involve various fluids and gases. If the stamping or printing requires multiple applications using different fluids, then the fluid is changed in operation 612. In some embodiments, the sensing surface on the device area may be treated first using one fluid and chemistry, and receptors attached using another fluid and chemistry. For example, in order to use self-assembled monolayer (SAM) of molecules, a first step may be to stamp a pattern to treat the sensing surface. A next step may be to attach head groups of silane groups, silyl groups, silanol groups, phosphonate groups, amine groups, thiol groups, alkyl groups, alkene groups, alkyne groups, azido groups, or epoxy groups. After the head groups are formed then, the receptors are attached to the head groups of SAM. If the fluid is changed in operation 612, then the process follows the dotted line back to operation 608.

In operation 614, the integrated electro-microfluidic probe card is dismounted from the device area and moved to the next device area. Operation 614 is the same as operation 520 of FIG. 5.

An aspect of this description relates to a method. The method includes mounting an integrated electro-microfluidic probe card to a device area on a bio-sensor device wafer, wherein the electro-microfluidic probe card has a first major surface and a second major surface opposite the first major surface. The method further includes electrically connecting at least one electronic probe tip extending from the first major surface to a corresponding conductive area of the device area. The method further includes stamping a test fluid onto the device area. The method further includes measuring via the at least one electronic probe tip a first electrical property of one or more bio-FETs of the device area based on the test fluid. In some embodiments, electrically connecting the at least one electronic probe tip to the corresponding conductive area includes electrically connecting the at least one electronic probe tip to a location beyond a boundary of the test fluid. In some embodiments, the method further includes marking the device area based on results of the measuring of the first electrical property. In some embodiments, the marking includes physically marking the device area. In some embodiments, the marking includes tracking a location of the device area. In some embodiments, the method further includes removing the device area from a manufacturing process in response to marking the device area as not passing. In some embodiments, the method further includes further processing the device area in response to marking the device area as not passing.

An aspect of this description relates to a method. The method further includes mounting an integrated electro-microfluidic probe card to a device area on a bio-sensor device wafer, wherein the electro-microfluidic probe card has a first major surface and a second major surface opposite the first major surface. The method further includes electrically connecting an electronic probe tip extending from the first major surface of the integrated electro-microfluidic probe card to a conductive area of the device area. The method further includes printing a test fluid onto the device area. The method further includes measuring via the electronic probe tip a first electrical property of one or more bio-FETs of the device area based on the test fluid. In some embodiments, the method further includes dismounting the integrated electro-microfluidic probe card from the device area following the measuring. In some embodiments, the measuring includes exposing the device area to light radiation. In some embodiments, the method further includes marking the device area based on results of the measuring of the first electrical property. In some embodiments, the method further includes removing the test fluid from the device area. In some embodiments, removing the test fluid includes removing the test fluid using a fluid or a gas.

An aspect of this description relates to a method. The method further includes mounting an integrated electro-microfluidic probe card to a device area on a bio-sensor device wafer, wherein the electro-microfluidic probe card has a first major surface and a second major surface opposite the first major surface. The method further includes electrically connecting at least one electronic probe tip extending from the first major surface to a corresponding conductive area of the device area. The method further includes placing a first test fluid on the device area, wherein the placing of the test fluid comprises stamping or printing. The method further includes measuring via the at least one electronic probe tip a first electrical property of one or more bio-FETs of the device area based on the first test fluid. In some embodiments, the method further includes removing the first test fluid from the device area following the measuring. In some embodiments, the method further includes placing a second test fluid on the device area, wherein the second test fluid is different from the first test fluid. In some embodiments, placing of the second test fluid includes stamping or printing the second test fluid. In some embodiments, the method further includes measuring via the at least one electronic probe tip a second electrical property of the one or more bio-FETs of the device area based on the second test fluid. In some embodiments, the method further includes marking the device area based on results of the measuring of the first electrical property and the measuring of the second electrical property. In some embodiments, the marking includes physically marking the device area.

In describing one or more of these embodiments, the present disclosure may offer several advantages over prior art devices. In the discussion of the advantages or benefits that follows it should be noted that these benefits and/or results may be present is some embodiments, but are not required in every embodiment. Further, it is understood that different embodiments disclosed herein offer different features and advantages, and that various changes, substitutions and alterations may be made without departing from the spirit and scope of the present disclosure.

What is claimed is:

1. A method comprising:
    mounting an integrated electro-microfluidic probe card to a device area on a bio-sensor device wafer, wherein the electro-microfluidic probe card has a first major surface and a second major surface opposite the first major surface, and the electro-microfluidic probe card comprises a transparent portion;
    electrically connecting at least one electronic probe tip extending from the first major surface to a corresponding conductive area of the device area;
    stamping a test fluid onto the device area, wherein the stamped test fluid is removable;
    measuring via the at least one electronic probe tip a first electrical property of one or more bio-FETs of the device area based on the test fluid; and
    flushing the stamped test fluid to remove the stamped test fluid from the device area.

2. The method of claim 1, wherein electrically connecting the at least one electronic probe tip to the corresponding conductive area comprises electrically connecting the at least one electronic probe tip to a location beyond a boundary of the test fluid.

3. The method of claim 1, further comprising marking the device area as passing or not passing based on results of the measuring of the first electrical property.

4. The method of claim 3, wherein the marking comprises physically marking the device area.

5. The method of claim 3, wherein the marking comprises tracking a location of the device area.

6. The method of claim 3, further comprising removing the device area from a manufacturing process in response to marking the device area as not passing.

7. The method of claim 3, further comprising further processing the device area in response to marking the device area as not passing.

8. A method comprising:
mounting an integrated electro-microfluidic probe card to a device area on a bio-sensor device wafer, wherein the electro-microfluidic probe card has a first major surface and a second major surface opposite the first major surface, and the electro-microfluidic probe card comprises a transparent portion;
electrically connecting an electronic probe tip extending from the first major surface of the integrated electro-microfluidic probe card to a conductive area of the device area;
printing a test fluid onto the device area, wherein the printed test fluid is removable;
measuring via the electronic probe tip a first electrical property of one or more bio-FETs of the device area based on the test fluid; and
flushing the printed test fluid to remove the printed test fluid from the device area.

9. The method of claim 8, further comprising dismounting the integrated electro-microfluidic probe card from the device area following the measuring.

10. The method of claim 8, wherein the measuring comprises exposing the device area to light radiation.

11. The method of claim 8, further comprising marking the device area based on results of the measuring of the first electrical property.

12. The method of claim 8, further comprising printing a second test fluid on the device area.

13. The method of claim 8, wherein flushing the test fluid comprises flushing the test fluid using a fluid or a gas.

14. A method comprising:
mounting an integrated electro-microfluidic probe card to a device area on a bio-sensor device wafer, wherein the electro-microfluidic probe card has a first major surface and a second major surface opposite the first major surface, and the electro-microfluidic probe card comprises a transparent portion;
electrically connecting at least one electronic probe tip extending from the first major surface to a corresponding conductive area of the device area;
placing a first test fluid on the device area, wherein the placing of the test fluid comprises stamping or printing, and the test fluid placed on the device area is removable;
measuring via the at least one electronic probe tip a first electrical property of one or more bio-FETs of the device area based on the first test fluid; and
removing an entirety of the first test fluid from the device area.

15. The method of claim 14, wherein removing the first test fluid from the device area comprises flushing the device area with fluid.

16. The method of claim 15, further comprising placing a second test fluid on the device area, wherein the second test fluid is different from the first test fluid.

17. The method of claim 16, wherein the placing of the second test fluid comprises stamping or printing the second test fluid.

18. The method of claim 16, further comprising measuring via the at least one electronic probe tip a second electrical property of the one or more bio-FETs of the device area based on the second test fluid.

19. The method of claim 18, further comprising marking the device area based on results of the measuring of the first electrical property and the measuring of the second electrical property.

20. The method of claim 19, wherein the marking comprises physically marking the device area.

* * * * *